(12) United States Patent
Schein et al.

(10) Patent No.: US 11,583,244 B2
(45) Date of Patent: Feb. 21, 2023

(54) SYSTEM AND METHODS FOR TRACKING ANATOMICAL FEATURES IN ULTRASOUND IMAGES

(71) Applicant: GE Precision Healthcare LLC, Milwaukee, WI (US)

(72) Inventors: Sagi Schein, Kiryat Tivon (IL); Doron Shaked, Tivon (IL); Ruth Bergman, Haifa (IL); Naomi Sato, Tokyo (JP); Menachem Halmann, Monona, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 568 days.

(21) Appl. No.: 16/593,854

(22) Filed: Oct. 4, 2019

(65) Prior Publication Data
US 2021/0100526 A1    Apr. 8, 2021

(51) Int. Cl.
| | | |
|---|---|---|
| *A61B 8/08* | (2006.01) | |
| *G06T 7/73* | (2017.01) | |
| *G06T 7/246* | (2017.01) | |
| *G06K 9/78* | (2006.01) | |
| *G06T 7/215* | (2017.01) | |

(Continued)

(52) U.S. Cl.
CPC .............. *A61B 8/085* (2013.01); *A61B 8/463* (2013.01); *A61B 8/5215* (2013.01); *G06T 7/11* (2017.01); *G06T 7/215* (2017.01); *G06T 7/248* (2017.01); *G06T 7/251* (2017.01); *G06T 7/75* (2017.01); *G06V 10/10* (2022.01); *G06T 2207/10132* (2013.01); *G06T 2207/20084* (2013.01); *G06V 2201/03* (2022.01)

(58) Field of Classification Search
CPC ....... A61B 8/085; A61B 8/463; A61B 8/5215; A61B 8/461; A61B 8/465; A61B 8/468; A61B 8/469; A61B 8/5207; A61B 8/5223; A61B 8/5276; A61B 8/5292; G06T 7/11; G06T 7/215; G06T 7/248; G06T 7/251; G06T 7/75; G06T 2207/10132; G06T 2207/20084; G06T 2207/10016; G06T 2207/20081; G06T 2207/30101; G06V 10/10; G06V 2201/03; G06V 10/454; G06K 9/6274
See application file for complete search history.

(56) References Cited

U.S. PATENT DOCUMENTS

| | | |
|---|---|---|
| 8,469,890 B2 | 6/2013 | Langeland et al. |
| 2016/0093046 A1* | 3/2016 | Jeon ....................... G16H 50/20 382/128 |

(Continued)

*Primary Examiner* — Joseph M Santos Rodriguez
*Assistant Examiner* — Kaitlyn E Sebastian
(74) *Attorney, Agent, or Firm* — McCoy Russell LLP

(57) ABSTRACT

Methods and systems are provided for tracking anatomical features across multiple images. One example method includes outputting, for display on a display device, an annotation indicative of a first location of an identified anatomical feature of a first ultrasound image, the annotation generated based on a first output of a model and outputting, for display on the display device, an adjusted annotation based on a second output of the model, the second output of the model generated based on a second ultrasound image and further based on the first output of the model, the adjusted annotation indicative of a second location of the identified anatomical feature in the second ultrasound image.

18 Claims, 9 Drawing Sheets

(51) Int. Cl.
    *G06T 7/11*     (2017.01)
    *A61B 8/00*     (2006.01)
    *G06V 10/10*     (2022.01)

(56) References Cited

U.S. PATENT DOCUMENTS

| | | | |
|---|---|---|---|
| 2017/0071571 A1* | 3/2017 | Lee | A61B 8/466 |
| 2018/0220995 A1* | 8/2018 | Pelissier | A61B 8/5207 |
| 2018/0325496 A1* | 11/2018 | Steininger | G06T 19/00 |
| 2018/0330518 A1* | 11/2018 | Choi | G16H 30/20 |
| 2019/0333227 A1* | 10/2019 | Zhang | G06T 7/149 |
| 2020/0242734 A1* | 7/2020 | Wang | G06N 20/10 |

* cited by examiner

SYSTEM AND METHODS FOR TRACKING ANATOMICAL FEATURES IN ULTRASOUND IMAGES

TECHNICAL FIELD

Embodiments of the subject matter disclosed herein relate to ultrasound imaging, and more particularly, to systems and methods for tracking identified features across multiple ultrasound images.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be displayed on a display device in real time or near real time, which may assist a clinician performing a medical procedure on the patient.

SUMMARY

In one embodiment, a method includes outputting, for display on a display device, an annotation indicative of a first location of an identified anatomical feature of a first ultrasound image, the annotation generated based on a first output of a model and outputting, for display on the display device, an adjusted annotation based on a second output of the model, the second output of the model generated based on a second ultrasound image and further based on the first output of the model, the adjusted annotation indicative of a second location of the identified anatomical feature in the second ultrasound image.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
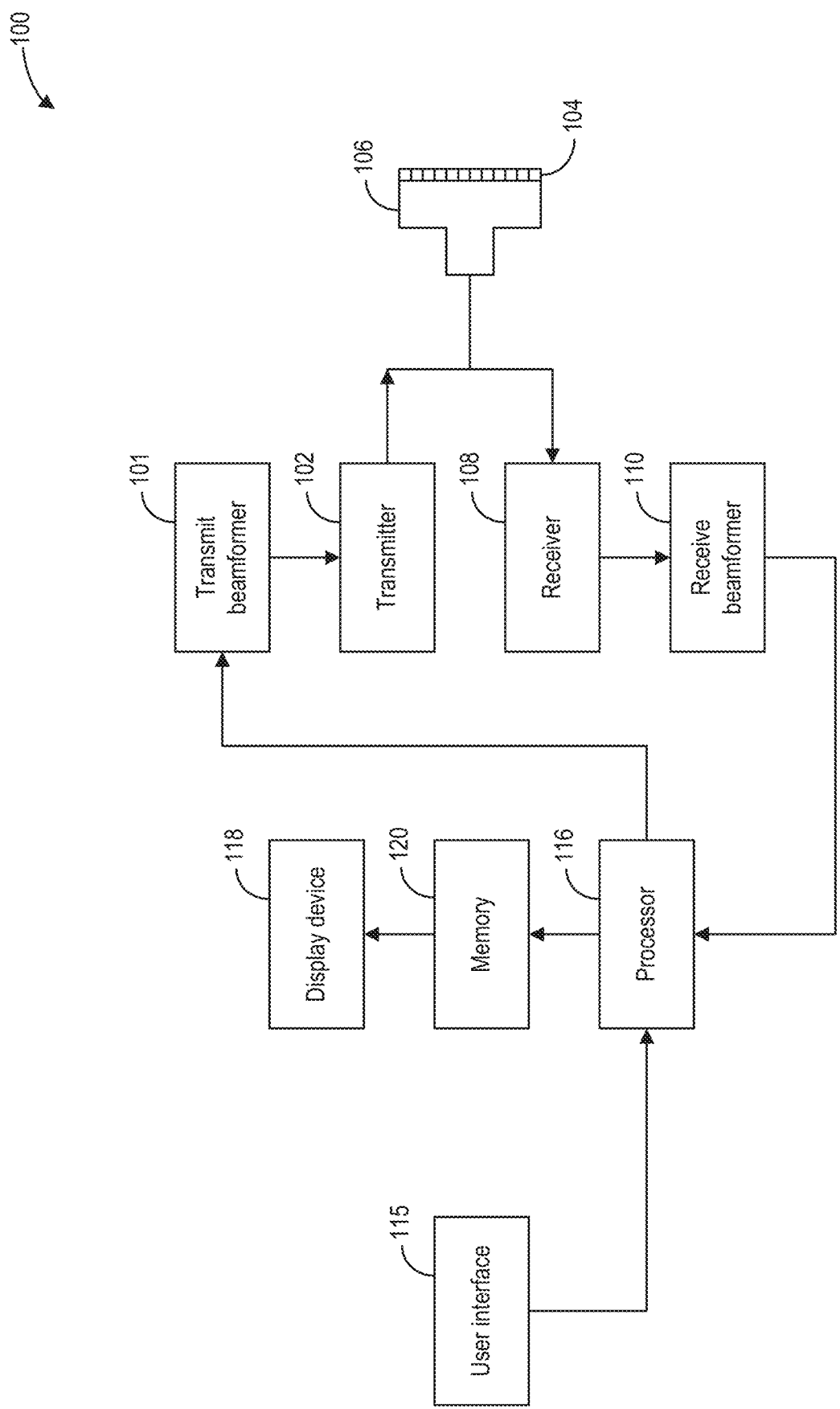
FIG. 1 shows a block diagram of an exemplary embodiment of an ultrasound system.

The following description relates to various embodiments for tracking features, such as anatomical features, across multiple frames of ultrasound imaging data. Ultrasound imaging may be used to assist in various medical procedures, such as needle insertion during delivery of anesthesia, where a needle may be inserted into the fascia of a patient surrounding a nerve where anesthetic material will be administered. A clinician such as an anesthesiologist may rely on the images obtained by the ultrasound imaging system to determine where to insert the needle, for example. Missing the correct location can result in slow or failed anesthesia. Often, the view interpretation (e.g., identification of the visible organs) of the ultrasound images is a visually intensive process for the clinician involving nuanced analyses such as which groups of otherwise similar textures move together. To make and keep the interpretation, the clinician needs to keep his or her eyes glued to the screen so as not to lose the relevant textures constituting the interpretation. If the clinician looks at the patient or attends to the anesthetic procedure being performed, the clinician may lose the visual interpretation and may need to reorient themselves, which could waste time and harm the procedure being performed.

Thus, according to embodiments disclosed herein, identified anatomical features of a patient may be tracked across multiple ultrasound images, even if the anatomical features morph or otherwise change in visual appearance due to patient movement or movement of an ultrasound probe of the ultrasound imaging system. The identified features may be visualized on the ultrasound images via suitable annotations that follow the tracked features, such as colored overlays or lines on the images, thereby allowing a clinician to quickly determine the location of various anatomical features in the images. By making a visual interpretation of the anatomy and keeping the interpretation stable on the anatomy as it moves and morphs in the view, the clinician may have a clear indication of where the anatomy is located and may be immediately well oriented even after looking away from the screen where the images are displayed.

To identify and track the anatomical features, the embodiments disclosed herein may utilize a machine learning model, such as a neural network, trained to identify (segment) anatomical parts of interest in the ultrasound view, and to track those identifications from frame to frame using a feedback mechanism. For example, the model may include a convolutional neural network trained to identify nerves, vessels, and bones in ultrasound image views typically associated with anesthesia delivery. The feedback may be entered by adding an additional input to the network. For every frame of ultrasound imaging data that is analyzed by the model, the detection output of the previous frame is added. The feedback may be added to the network as either as another layer of the input image (at the same resolution), or in the most bottom (down-sampled) layer of the network, as the bottom layer may include the semantics of the rough segmentation, which is semantically compatible to the segmentation results of the previous frame.

In this way, for example, an organ previously detected in an image with high confidence may be used as feedback to the system to re-identify the same organ at the same location in a current image even when the current image does not clearly indicate the anatomy. This supports a new workflow where the ultrasound operator/clinician may lift his or her eyes from the screen for a short while having confidence that the anatomic interpretation previously viewed will be there/indicated when the operator/clinician looks back to the ultrasound image. On the display, organs or other anatomical features may be marked/annotated (e.g. highlighted as a color tint to the ultrasound image), and the anatomic interpretation of the image is stabilized on the anatomic content. In addition, degrees of confidence may be displayed (e.g., by modulating the color saturation or bold-lining the segmented anatomy). For example, an indicator of confidence in the provided interpretation may be displayed along with the images and associated annotations, thereby increasing the confidence in the stability of the interpretation. In addition, an interface may be provided to receive input from the user to the system marking or approving an organ location and marking it for tracking. For example, a user interface may be displayed whereby a user (e.g., operator/clinician) can indicate to the system that the current interpretation is correct and should be maintained, and thus should be kept as the reference to which the confidence measure relates.

Figure 2:
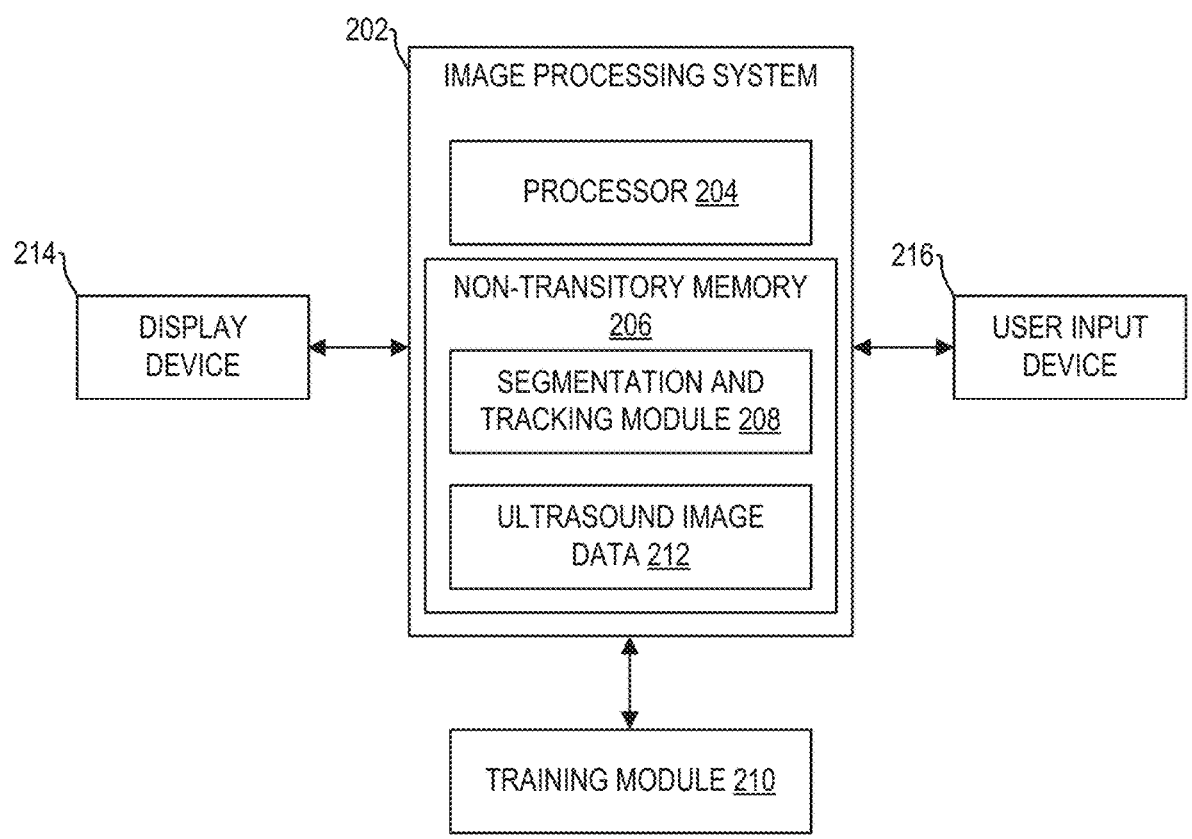
FIG. 2 is a schematic diagram illustrating a system for segmenting and tracking features across multiple images, according to an exemplary embodiment.
Figure 7:
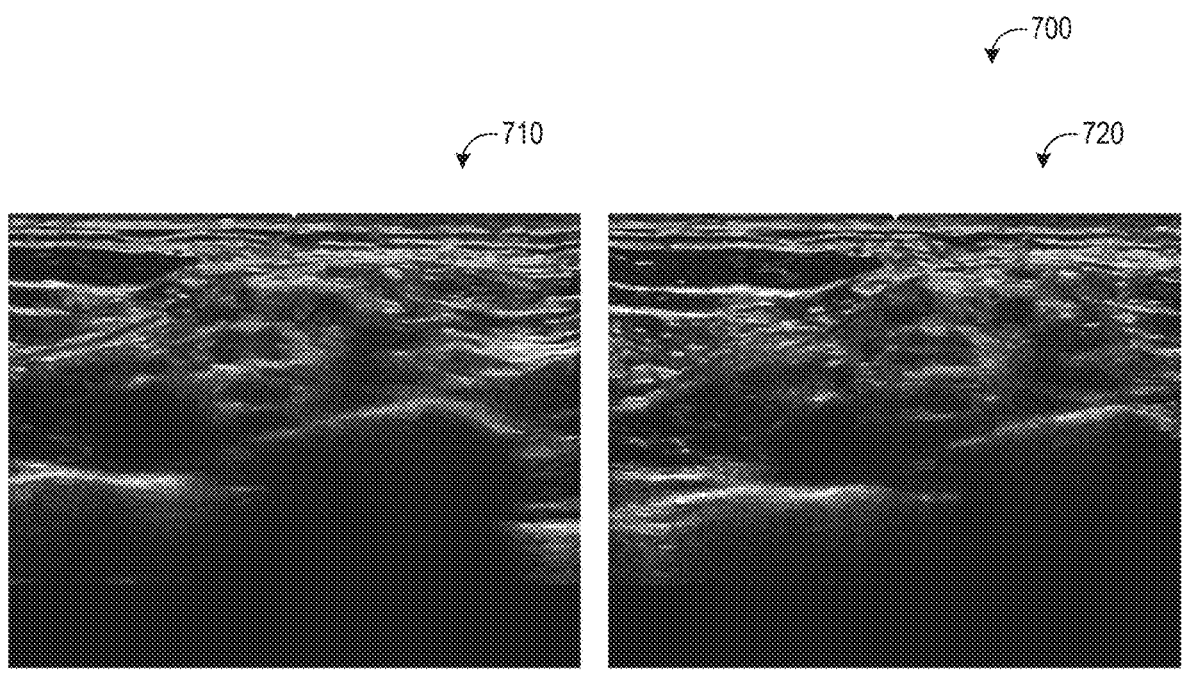
FIG. 7 shows two frames of ultrasound image data without identified features tracked and labeled.
Figure 8:
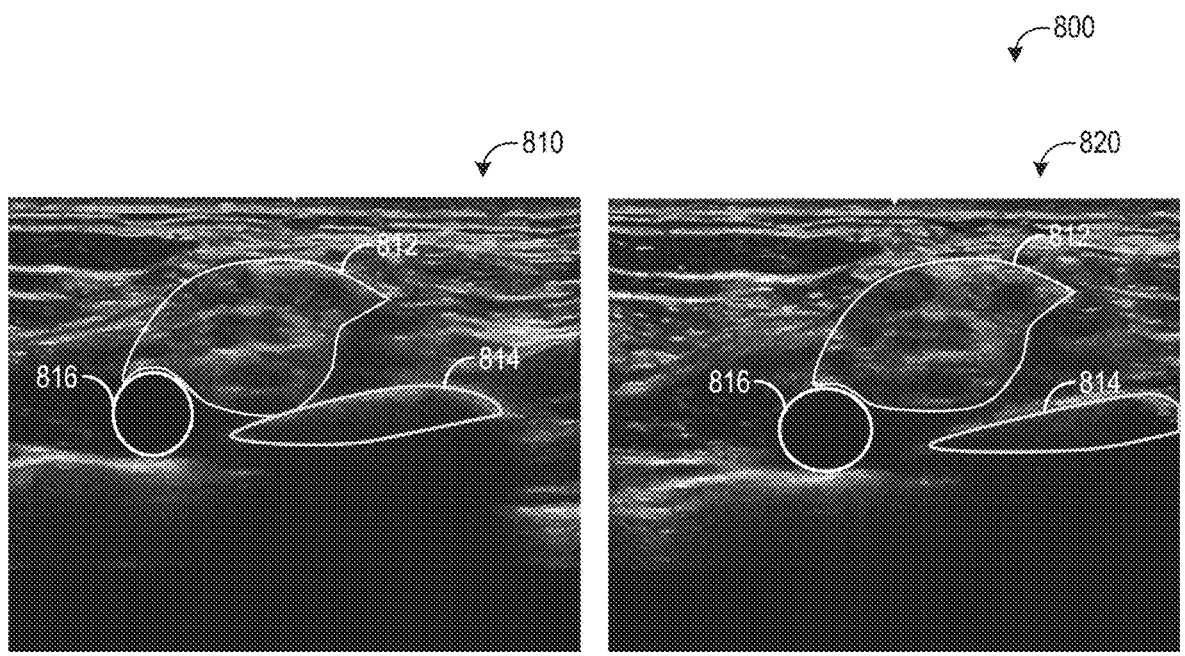
FIG. 8 shows the two frames of ultrasound image data of FIG. 7 with identified features tracked and labeled.

An example ultrasound system including an ultrasound probe, a display device, and an imaging processing system are shown in FIG. 1. Via the ultrasound probe, ultrasound images may be acquired and displayed on the display device. The displayed images may be annotated with annotations that are generated using a segmentation and tracking model that may identify anatomical features in the ultrasound images and track the location of the identified anatomical features across multiple ultrasound images. The segmentation and tracking model may be stored on and executed by the image processing system, as shown in FIG. 2. In some examples, the segmentation and tracking model may a convolution neural network (CNN), such as the CNN shown in FIG. 3 or the CNN shown in FIG. 4. The segmentation and tracking model may be deployed to identify and track anatomical features in ultrasound images, according to the method shown in FIGS. 5A and 5B. The segmentation and tracking model may be trained according to the method shown in FIG. 6, at least in some examples. FIG. 7 shows a pair of ultrasound images including three anatomical features of relevance, without annotations indicative of the locations of the anatomical features. FIG. 8 shows the images of FIG. 7 with annotations indicative of the locations of the anatomical features, where the annotations are generated according to output from the segmentation and tracking model. FIG. 8 shows an image with annotations indicative of the locations of the anatomical features, where one of the annotations is modified to notify a user of a warning condition.

Referring to FIG. 1, a schematic diagram of an ultrasound imaging system 100 in accordance with an embodiment of the invention is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be segmented by a machine learning model trained using ultrasound images and corresponding ground truth output. As used herein, ground truth output refers to an expected or "correct" output based on a given input into a machine learning model. For example, if a machine learning model is being trained to classify images of cats, the ground truth output for the model, when fed an image of a cat, is the label "cat".

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/communicatively coupled to a user input device 214 and a display device 216.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store segmentation and tracking module 208 and ultrasound image data 212. Segmentation and tracking module 208 may include one or more machine learning models, such as deep learning networks, comprising a plurality of weights and biases, activation functions, loss functions, gradient descent algorithms, and instructions for implementing the one or more deep neural networks to process input ultrasound images. For example, segmentation and tracking module 208 may store instructions for implementing a neural network, such as the convolutional neural network (CNN) 300, shown in FIG. 3, or the CNN 400 shown in FIG. 4. Segmentation and tracking module 208 may include trained and/or untrained neural networks and may further include training routines, or parameters (e.g., weights and biases), associated with one or more neural network models stored therein.

Image processing system 202 may be communicatively coupled to training module 210, which comprises instructions for training one or more of the machine learning models stored in segmentation and tracking module 208. Training module 210 may include instructions that, when executed by a processor, cause the processor to conduct one or more of the steps of method 600, discussed in more detail below. In one example, training module 210 includes instructions for receiving training data sets from ultrasound image data 212, which comprise sets of ultrasound images, associated ground truth labels/images, and associated model outputs for use in training one or more of the machine learning models stored in segmentation and tracking module 208. Training module 210 may receive ultrasound images, associated ground truth labels/images, and associated model outputs for use in training the one or more machine learning models from sources other than ultrasound image data 212, such as other image processing systems, the cloud, etc. In some embodiments, one or more aspects of training module 210 may include remotely-accessible networked storage devices configured in a cloud computing configuration. Non-transitory memory 206 may further store ultrasound image data 212, such as ultrasound images captured by the ultrasound imaging system of FIG. 1. For example, ultrasound image data 212 may store ultrasound images, ground truth output, iterations of machine learning model output, and other types of ultrasound image data. In some embodiments, ultrasound image data 212 may store ultrasound images and ground truth output in an ordered format, such that each ultrasound image is associated with one or more corresponding ground truth outputs.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 216 may comprise one or more of a touchscreen, a keyboard, a mouse, a trackpad, a motion sensing camera, or other device configured to enable a user to interact with and manipulate data within image processing system 31. In one example, user input device 216 may enable a user to make a selection of an ultrasound image to use in training a machine learning model, or for further processing using a trained machine learning model.

Display device 214 may include one or more display devices utilizing virtually any type of technology. In some embodiments, display device 214 may comprise a computer monitor, and may display ultrasound images. Display device 214 may be combined with processor 204, non-transitory memory 206, and/or user input device 216 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
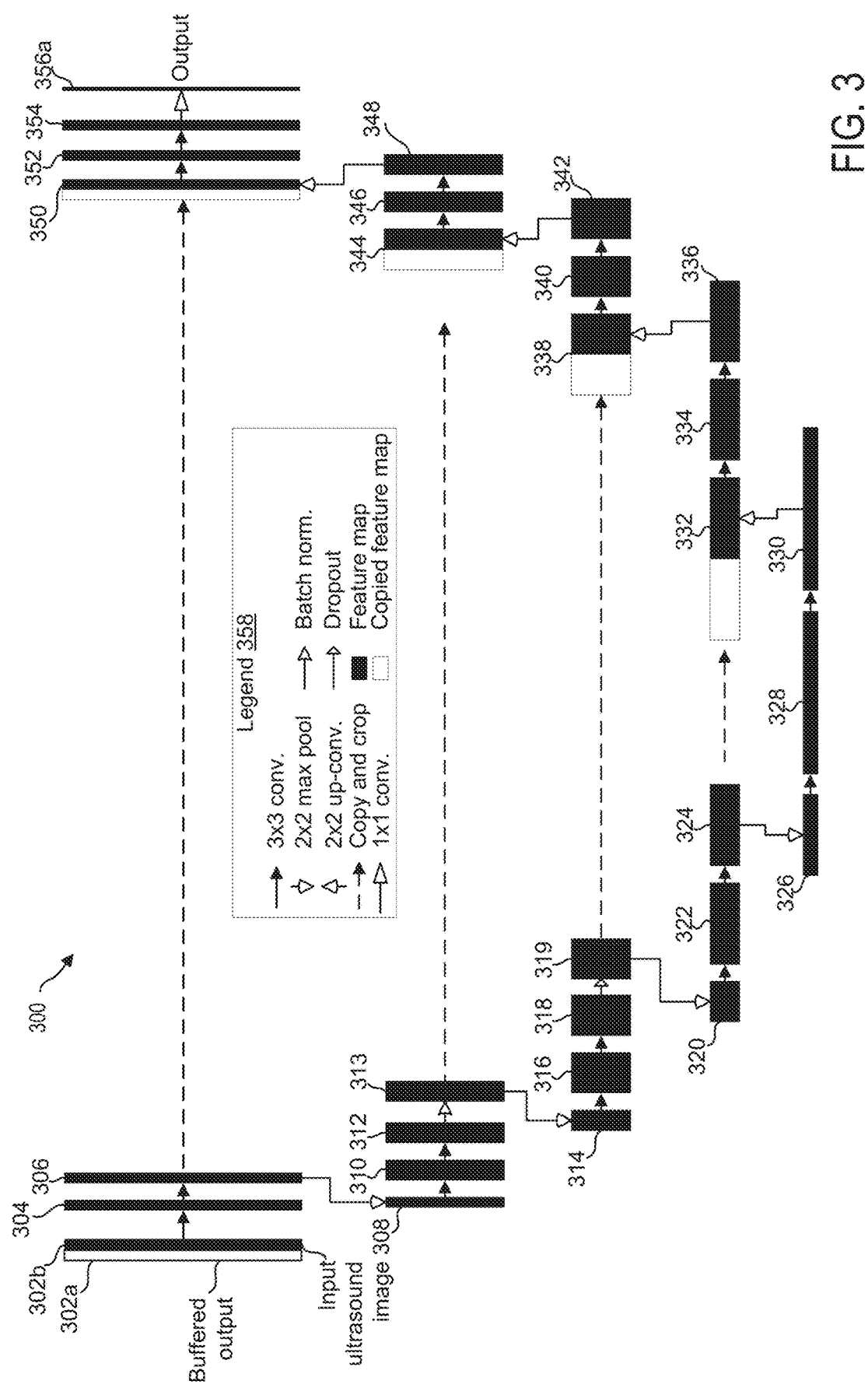
FIG. 3 is a schematic diagram illustrating a layout of a deep learning network which may use output of the network as feedback to the network, according to a first exemplary embodiment.

Turning to FIG. 3, architecture for an example convolutional neural network (CNN) 300 is shown. CNN 300 represents one example of a machine learning model according to the current disclosure, wherein the parameters of CNN 300 may be learned using training data produced according to one or more methods disclosed herein. CNN 300 comprises a U-net architecture, which may be divided into an autoencoder portion (descending portion, elements 302b-330) and an autodecoder portion (ascending portion, elements 332-356a). CNN 300 is configured to receive ultrasound images comprising a plurality of pixels/voxels, and map the input ultrasound image to a pre-determined type of output. CNN 300 includes a series of mappings, from an input image tile 302b which may be received by an input layer, through a plurality of feature maps, and finally to an output layer 356a.

The various elements comprising CNN 300 are labeled in legend 358. As indicated by legend 358, CNN 300 includes a plurality of feature maps (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, and depth, wherein the dimensions refer to the number of neurons comprising the feature map (e.g., how many neurons long, how many neurons wide, and how many neurons deep, a specified feature map is).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN.

The transformations/mappings performed by each feature map are indicated by arrows, wherein each type of arrow corresponds to a distinct transformation, as indicated by legend 358. Rightward pointing solid black arrows indicate 3×3 convolutions with stride of one, wherein output from a 3×3 grid of feature channels of an immediately preceding feature map are mapped to a single feature channel of a current feature map. Each 3×3 convolution may be followed by an activation function, wherein, in one embodiment, the activation function comprises a rectified linear unit (ReLU).

Downward pointing hollow arrows indicate 2×2 max pooling, wherein the max value from a 2×2 grid of feature channels is propagated from an immediately preceding feature map to a single feature channel of a current feature map, thereby resulting in a 4-fold reduction in spatial resolution of the immediately preceding feature map.

Upward pointing hollow arrows indicate 2×2 up-convolutions, which comprise mapping output from a single feature channel of an immediately preceding feature map to a 2×2 grid of feature channels in a current feature map, thereby increasing the spatial resolution of the immediately preceding feature map 4-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map are equal, no cropping may be performed.

Rightward pointing arrows with hollow elongated triangular heads indicate a 1×1 convolution, in which each feature channel in an immediately preceding feature map is mapped to a single feature channel of a current feature map, or in other words, wherein a 1-to-1 mapping of feature channels between an immediately preceding feature map and a current feature map occurs.

Rightward pointing arrows with arcuate hollow heads indicate batch normalization operations, wherein a distribution of activations of an input feature map are normalized. Rightward pointing arrows with a short hollow triangular head indicates a dropout operation, wherein random or pseudo-random dropout of input neurons (as well as their inputs and outputs) occurs during training.

In addition to the operations indicated by the arrows within legend 358, CNN 300 includes feature maps that are represented in FIG. 3 by solid filled rectangles, wherein feature maps comprise a height (top to bottom length as shown in FIG. 3, which corresponds to a y spatial dimension in an x-y plane), width (not shown in FIG. 3, assumed equal in magnitude to height, and corresponds to an x spatial dimension in an x-y plane), and depth (a left-right length as shown in FIG. 3, which corresponds to the number of features within each feature channel). Likewise, CNN 300 includes copied and cropped feature maps that are represented in FIG. 3 by hollow (unfilled) rectangles, wherein copied feature maps comprise height (top to bottom length as shown in FIG. 3, which corresponds to a y spatial dimension in an x-y plane), width (not shown in FIG. 3, assumed equal in magnitude to height, and corresponds to an x spatial dimension in an x-y plane), and depth (a length from a left side to a right side as shown in FIG. 3, which corresponds to the number of features within each feature channel).

Starting at input image tile 302b (herein also referred to as an input layer), data corresponding to an ultrasound image may be input and mapped to a first set of features. In some embodiments, the input data is pre-processed (e.g., normalized) before being processed by the neural network. The weights/parameters of each layer of CNN 300 may be learned during a training process, wherein matched pairs of input and expected output (ground truth output) are fed to CNN 300. Parameters may be adjusted based on a gradient descent algorithm, or other algorithm, until the output of CNN 300 matches the expected output (the ground truth output) within a threshold degree of accuracy.

As indicated by the solid black rightward pointing arrow immediately to the right of input image tile 302b, a 3×3 convolution of the feature channels of input image tile 302b (combined with feedback layer 302a, described in more detail below) is performed to produce feature map 304. As discussed above, a 3×3 convolution includes mapping input from a 3×3 grid of feature channels to a single feature channel of a current feature map, using learned weights, wherein the learned weights are referred to as a convolution filter. Each 3×3 convolution in CNN architecture 300 may include a subsequent activation function, which in one embodiment includes passing the output of each 3×3 convolution through a ReLU. In some embodiments, activation functions other than ReLUs may be employed, such as Softplus (also referred to as SmoothReLUs), leaky ReLUs, noisy ReLUs, exponential linear units (ELUs), Tanh, Gaussian, Sinc, Bent identity, logistic functions, and other activation functions known in the art of machine learning.

As indicated by the solid black rightward pointing arrow immediately to the right of feature map 304, a 3×3 convolution is performed on feature map 304 to produce feature map 306.

As indicated by the downward pointing arrow beneath feature map 306, a 2×2 max pooling operation is performed on feature map 306 to produce feature map 308. Briefly, a 2×2 max pooling operation includes determining a max feature value from a 2×2 grid of feature channels of an immediately preceding feature map, and setting a single feature, in a single feature channel, of a current feature map to the max value so determined. Additionally, feature map 306 is copied and concatenated with output from feature map 348 to produce feature map 350, as indicated by the dash-tailed rightward pointing arrow immediately to the right of feature map 306.

As indicated by the solid black rightward pointing arrow immediately to the right of feature map 308, a 3×3 convolution with stride 1 is performed on feature map 308 to produce feature map 310. As indicated by the solid black rightward pointing arrow immediately to the right of feature map 310, a 3×3 convolution with stride 1 is performed on feature map 310 to produce feature map 312.

As indicated by the rightward pointing hollow headed arcuate arrow immediately to the right of feature map 312, an optional batch normalization operation is conducted on the output of feature map 312 to produce feature map 313. In batch normalization, the outputs of feature map 312 are normalized across a mini-batch to speed up training of CNNs and reduce the sensitivity to network initialization. Batch normalization operations normalize the activations of each channel by subtracting the mini-batch mean and dividing by the mini-batch standard deviation. Then, the batch operation shifts the input by a learnable offset $\beta$ and scales it by a learnable scale factor $\gamma$.

As indicated by the downward pointing hollow headed arrow beneath feature map 313, a 2×2 max pooling operation is performed on feature map 313 to produce feature map 314, wherein feature map 314 is of one fourth the spatial resolution of feature map 312. Additionally, feature map 313 is copied and concatenated with output from feature map 342 to produce feature map 344, as indicated by the dash-tailed rightward pointing arrow immediately to the right of feature map 313.

As indicated by the solid black rightward pointing arrow immediately to the right of feature map 314, a 3×3 convolution with stride 1 is performed on feature map 314 to produce feature map 316. As indicated by the solid black rightward pointing arrow immediately to the right of feature map 316, a 3×3 convolution with stride 1 is performed on feature map 316 to produce feature map 318.

As indicated by the rightward pointing short hollow headed triangular arrow immediately to the right of feature map 318, an optional dropout operation is performed during training, wherein a random or pseudo random subset of input activations/features are removed/deleted for a given iteration of training, thereby reducing a probability of CNN 300 overfitting the training data.

As indicated by the downward pointing arrow beneath feature map 319, a 2×2 max pooling operation is performed on feature map 319 to produce feature map 320, wherein feature map 320 is of half the spatial resolution of feature map 319. Additionally, feature map 319 is copied and concatenated with output from feature map 336 to produce feature map 338, as indicated by the dash-tailed rightward pointing arrow immediately to the right of feature map 319.

As indicated by the solid black rightward pointing arrow immediately to the right of feature map 320, a 3×3 convolution with stride 1 is performed on feature map 320 to produce feature map 322. As indicated by the solid black rightward pointing arrow immediately to the right of feature map 322, a 3×3 convolution with stride 1 is performed on feature map 322 to produce feature map 324.

As indicated by the downward pointing arrow beneath feature map 324, a 2×2 max pooling operation is performed on feature map 324 to produce feature map 326, wherein feature map 326 is of one fourth the spatial resolution of feature map 324. Additionally, feature map 324 is copied and concatenated with output from feature map 330 to produce feature map 332, as indicated by the dash-tailed rightward pointing arrow immediately to the right of feature map 324.

As indicated by the solid black rightward pointing arrow immediately to the right of feature map 326, a 3×3 convolution is performed on feature map 326 to produce feature map 328. As indicated by the solid black rightward pointing arrow immediately to the right of feature map 328, a 3×3 convolution with stride 1 is performed on feature map 328 to produce feature map 330.

As indicated by the upward pointing arrow immediately above feature map 330, a 2×2 up-convolution is performed on feature map 330 to produce a first half of feature map 332, while copied features from feature map 324 are used to produce a second half of feature map 332. Briefly, a 2×2 up-convolution (herein also referred to as a deconvolution, or up-sampling) with stride of 2, includes mapping a single feature in a single feature channel of an immediately preceding feature map to four features distributed amongst four feature channels in a current feature map (that is, output from a single feature channel is taken as input by four feature channels). Up-convolution/deconvolution/up-sampling comprises projecting a feature value, from a single feature channel, through a deconvolution filter (also herein referred to as a deconvolution kernel) to produce a plurality of outputs.

As indicated by the solid black rightward pointing arrow immediately to the right of feature map 332, a 3×3 convolution is performed on feature map 332 to produce feature map 334.

As indicated in FIG. 3, a 3×3 convolution is performed on feature map 334 to produce feature map 336 and a 2×2 up convolution is performed on feature map 336 to produce half of feature map 338, while copied features from feature map 318 produce the second half of feature map 338. Further, a 3×3 convolution is performed on feature map 338 to produce feature map 340, a 3×3 convolution is performed on feature map 340 to produce feature map 342, and a 2×2 up convolution is performed on feature map 342 to produce a first half of feature map 344, while copied and cropped features from feature map 312 are used to produce the second half of feature map 344. A 3×3 convolution is performed on feature map 344 to produce feature map 346, a 3×3 convolution is performed on feature map 346 to produce feature map 348, and a 2×2 up convolution is performed on feature map 348 to produce a first half of feature map 350, while copied features from feature map 306 are used to produce the second half of feature map 350. A 3×3 convolution is performed on feature map 350 to produce feature map 352, a 3×3 convolution is performed on feature map 352 to produce feature map 354, and a 1×1 convolution is performed on feature map 354 to produce output layer 356a. Briefly, a 1×1 convolution includes a 1-to-1 mapping of feature channels in a first feature space to feature channels in a second feature space, wherein no reduction in spatial resolution occurs.

Output layer 356a may comprise an output layer of neurons, wherein each neuron may correspond to a pixel of a segmented ultrasound image, and wherein output of each neuron may correspond to a predicted anatomical feature (or lack of the anatomical feature) in a given location within the input ultrasound image. For example, the output of a neuron may indicate whether the corresponding pixel of segmented ultrasound image is part of a vessel, a nerve, a bone, an artery, etc., or part of an unidentified feature.

The output layer 356a may be fed back to an input layer of CNN 300. In the example shown in FIG. 3, the output layer from a previous iteration of CNN 300 is applied as input to a current iteration of CNN 300 as a feedback layer 302a. The feedback layer 302a may be included as another layer of the input image (at the same resolution) and thus may be included as part of input image tile 302b. For example, the input ultrasound image and the output layer of a previous iteration of CNN 300 (e.g., the buffered output, where buffered indicates that the output is stored in a buffer until it is used as an input to CNN 300) may be formed as a vector that is entered as input to CNN 300. In some examples, while not shown in FIG. 3, the input ultrasound image that was used as input in the previous iteration of CNN 300 may also be included in the input layer.

In some examples, the CNN may operate at a slower frame rate than the frame rate of the ultrasound system used to generate the ultrasound images that are input into CNN 300. For example, as explained above with respect to FIG. 1, the ultrasound system 100 may operate at a frame rate of 30 Hz. However, the CNN may operate with a frame rate of 6 Hz. That is, the CNN may produce an output based on an input ultrasound image, where the output is actually generated by the CNN after additional ultrasound images have been acquired. Thus, when a first ultrasound image is input into CNN 300, the output that is generated from CNN 300 based on the first ultrasound image may actually be applied to (e.g., annotations may be generated and overlaid on) a second ultrasound image acquired after the first ultrasound image. One or more intermediate ultrasound images may be acquired between acquisition of the first ultrasound image and acquisition of the second ultrasound image. Thus, as will be explained in more detail below, in some examples, a motion tracking algorithm may execute in parallel with the CNN, and if motion is detected between ultrasound image frames, the output of the CNN 300 may be adjusted based on the detected motion.

In this way, CNN 300 may enable mapping of an ultrasound image to an output. The architecture of CNN 300 illustrated in FIG. 3 includes the feature map transformations which occur as an input image tile is propagated through the neuron layers of the convolutional neural network, to produce predicted output.

The weights (and biases) of the convolutional layers in CNN 300 are learned during training, as will be discussed in more detail with reference to FIG. 6 below. Briefly, a loss function is defined to reflect the difference between the predicted output and the ground truth output. The difference/loss may be back projected to the CNN to update the weights (and biases) of the convolutional layers. A plurality of training data sets, comprising ultrasound images and corresponding ground truth outputs, may be used to train CNN 300.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 3, or may replace one or more of the shown layers/feature maps.

It should be understood that the architecture and configuration of CNN 300 shown in FIG. 3 is for illustration, not for limitation. Any appropriate neural network can be used, such as ResNet, recurrent neural networks, General Regression Neural Network (GRNN), etc. One or more specific embodiments of the present disclosure are described above in order to provide a thorough understanding. The skilled artisan will understand that specific details described in the embodiments can be modified when being placed into practice without deviating the spirit of the present disclosure.

Figure 4:
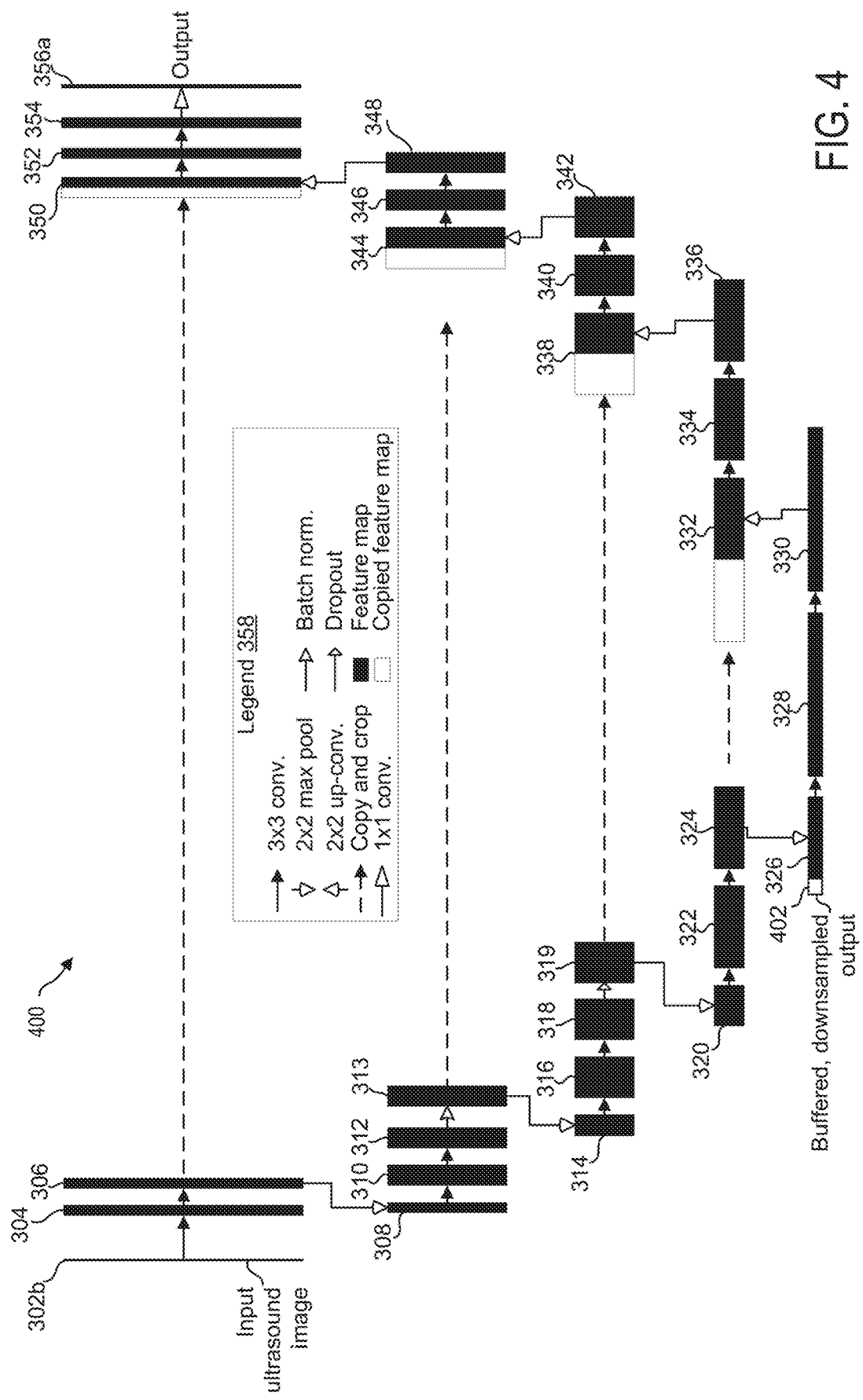
FIG. 4 is a schematic diagram illustrating a layout of a deep learning network which may use output of the network as feedback to the network, according to a second exemplary embodiment.

FIG. 4 shows architecture for CNN 400, which is another example of a machine learning model according to the current disclosure, wherein the parameters of CNN 400 may be learned using training data produced according to one or more methods disclosed herein. CNN 400 is similar to CNN 300, and as such represents a U-net architecture, which may be divided into an autoencoder portion (descending portion, elements 302$b$-330) and an autodecoder portion (ascending portion, elements 332-356$a$). Like components are numbered the same as in FIG. 3 and are not reintroduced.

In CNN 400, the output from CNN 400 (e.g., output layer 356$a$) may be fed back as input to a subsequent iteration of CNN 400 as a feedback layer 402. The feedback layer 402 may include a down-sampled version of output layer 356$a$ and may be included as part of feature map 326, which is the bottom layer of CNN 400 and as such may have the semantics of the rough segmentation, which may be semantically compatible to the segmentation results of the previous input ultrasound image frame. As indicated by the solid black rightward pointing arrow immediately to the right of feature map 326, a 3×3 convolution is performed on feature map 326 (including feedback layer 402) to produce feature map 328. By entering the output from CNN 400 as a down-sampled output to the bottom layer of CNN 400, the shapes of the anatomical features that are identified by the output of CNN 400 may be more consistent relative to the shapes of the anatomical features that are identified by the output of the CNN 300 of FIG. 3. However, the boundaries of the shapes of the anatomical features identified by the output of the CNN 300 of FIG. 3 may be smoother than the boundaries of the shapes of the anatomical features identified by the output of the CNN 400 of FIG. 4.

Figure 5A:
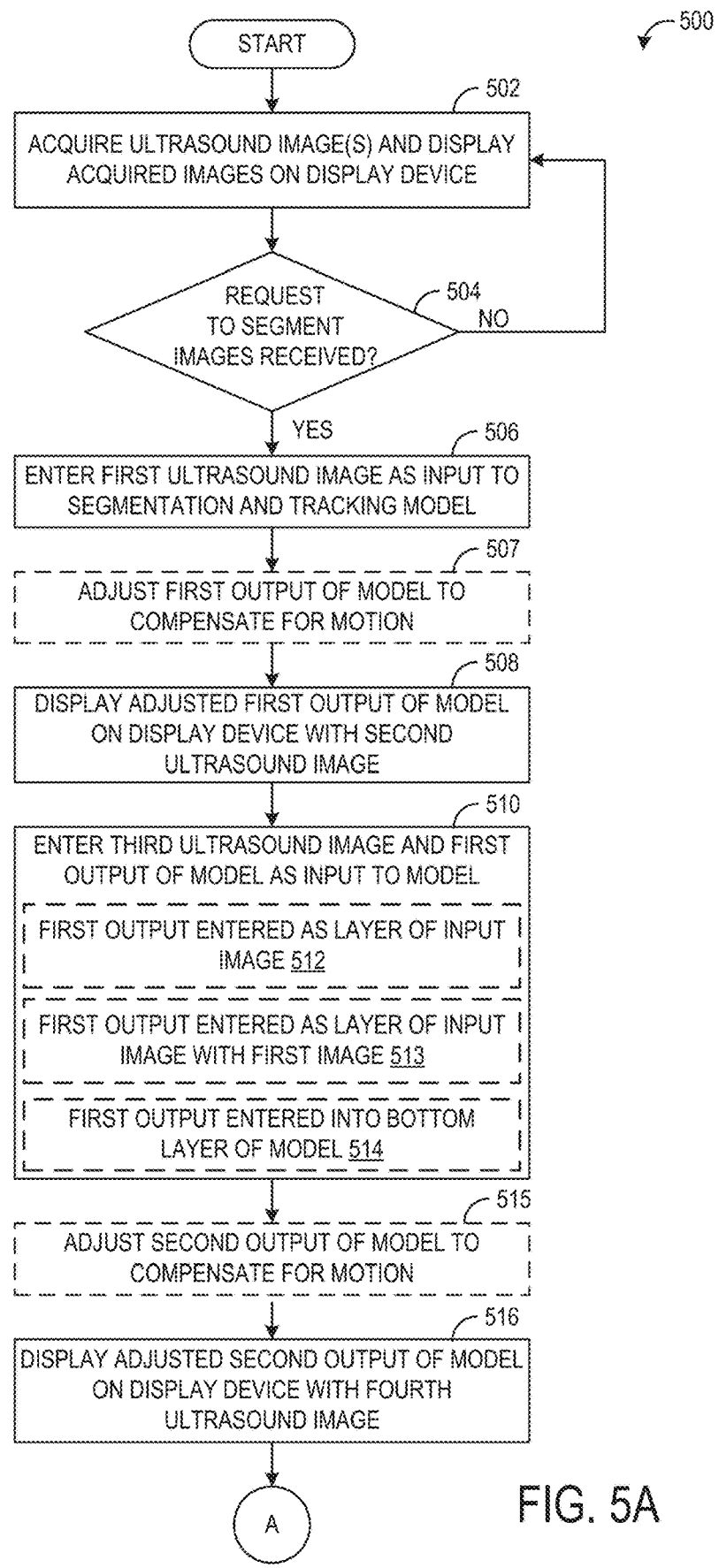
FIGS. 5A and 5B show a flow chart illustrating a method for segmenting and tracking features across multiple images using a segmentation and tracking model, according to an exemplary embodiment.
Figure 5B:
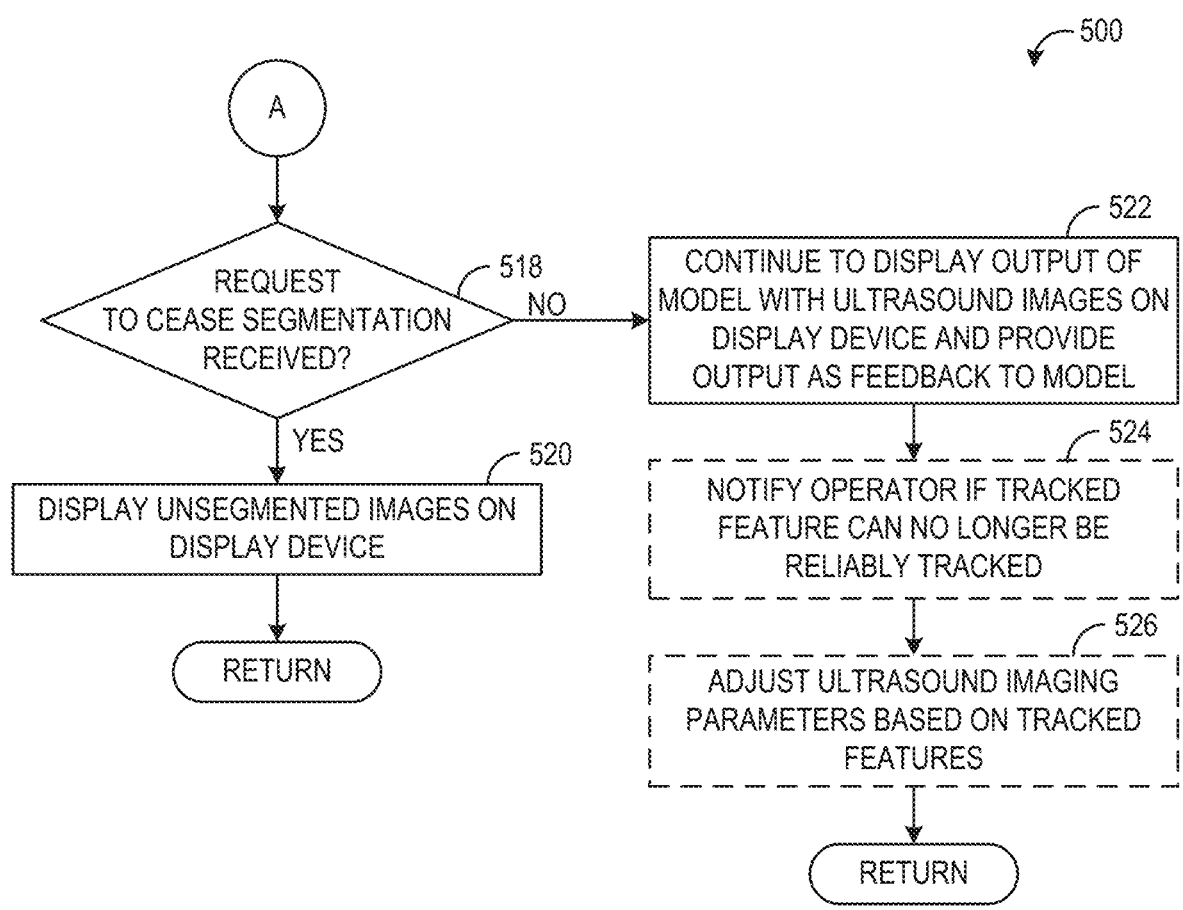

Referring to FIGS. 5A and 5B, a flow chart of a method 500 for segmenting and tracking features in ultrasound images is shown. Method 500 may be implemented by one or more of the above disclosed systems, such as image processing system 202 and/or ultrasound system 100.

At 502, ultrasound images are acquired via an ultrasound system (e.g., system 100 of FIG. 1) and displayed on a display device (e.g., display device 118 of FIG. 1). To acquire the images, an ultrasound probe of the ultrasound system (e.g., probe 106) may be controlled to output ultrasound signals (e.g., via energization of the ultrasound transducers of the ultrasound probe) to an imaging subject (such as a patient) and receive the resultant echoes (e.g., where the output acoustic signals are backscattered from the imaging subject). The signals received by the ultrasound probe are then processed by the ultrasound system to generate the ultrasound images that are output for display. The ultrasound images may be acquired and displayed at a suitable frame rate, such as 30 Hz.

At 504, method 500 determines if a request to segment subsequent ultrasound images is received. Segmenting ultrasound images may include identifying one or more anatomical features in the ultrasound images and including an indication of the identification, location, boundaries, and/or other features of each identified anatomical feature on the ultrasound images. In some examples, the request to segment the ultrasound images may be received from a user. For example, an operator of the ultrasound system (e.g., a sonographer or other clinician such as an anesthesiologist) may enter an input via a user interface (e.g., user interface 115) or via the probe requesting the subsequent acquired ultrasound images be segmented. In other examples, the request to segment the ultrasound images may be automatic, e.g., the ultrasound system may follow a scanning workflow selected by the user at the time of initiation of an ultrasound scanning session, and the scanning workflow may dictate that the acquired ultrasound images be segmented. It is to be understood that the request to segment the ultrasound images may be received before acquisition of the ultrasound images has commenced.

If a request to segment the ultrasound images has not been received, method 500 proceeds to 502 to acquire and display ultrasound images, without segmenting the acquired ultrasound images. For example, the acquired ultrasound images may be displayed without indications of identified anatomical features, such as the ultrasound images shown in FIG. 7 and described in more detail below. If the request to segment the ultrasound images has been received, method 500 proceeds to 506 to enter a first ultrasound image as input to a segmentation and tracking model. In some embodiments, the segmentation and tracking model is a CNN, having an autoencoder-autodecoder type architecture, such as CNN 300 shown in FIG. 3 or CNN 400 shown in FIG. 4. The segmentation and tracking model may generate, as a first output, an identity and/or location of one or more anatomical features in the first ultrasound image.

In some examples, method 500 may optionally include, at 507, adjusting first output of the model based on tracked motion. The segmentation and tracking model may generate output at a slower rate than the ultrasound images are acquired. For example, the segmentation and tracking model may generate an output at a rate that is one-fifth of the rate of ultrasound image acquisition. As a result, the first output of the model may be generated well after the first ultrasound image is acquired, and one or more additional ultrasound images may be acquired between acquisition of the first ultrasound image and generation of the first output. This may lead to the output of the model (e.g., the annotations generated based on the output) being displayed with respect to images that have been obtained after the input image used to generate the output. If little to no motion of the imaged anatomical features is occurring over this time, the annotations may still accurately reflect the locations of the anatomical features. However, if the anatomical features are moving across the images (e.g., due to patient movement, respiration, or heartbeat, or due to movement of the probe or changes in probe imaging parameters such as frequency or depth), the annotations may begin to lose accuracy, as the annotations may remain fixed in place while the underlying anatomical features move (at least until the next output of the model is generated and output). Accordingly, a separate motion tracker may be executed in parallel with the segmentation and tracking model. The motion tracker may analyze each image and determine an overall level of motion for each image as an entirety (e.g., relative to a previous image) or determine a level of motion for individual anatomical features in each image (e.g., relative to the features in a previous image). The motion tracker may determine motion (whether for an entire image or for each separate identified feature of an image) using a suitable technique, such as changes in pixel brightness, movement of an associated tracking boundary for each identified feature, changes in edges of identified features, or the like.

If the motion tracker detects motion of one or more anatomical features across two or more images, the first output may be adjusted based on the determined motion. For example, as explained above, the first output (e.g., the annotations generated based on the first output) may be displayed on multiple images before the second output is generated. If the motion tracker detects motion in these images, the first output may be updated based on the detected motion. For example, if the motion tracker determines that the entire field of view of the ultrasound probe has shifted (e.g., due to the operator moving the probe) one mm to the left, the annotations may be shifted one mm to the left. If the motion tracker determines that an identified anatomical feature is moving (e.g., periodic motion due to patient respiration or heartbeat), the annotation for that anatomical feature may be adjusted accordingly (e.g., the annotation may change in size, shape, and/or location).

Additionally, in some examples, when motion is detected by the motion tracker, an image used as input to the segmentation and tracking model may be updated based on the motion. Because of the delay between when the input image is acquired and when the output of the model is generated based on that image, the output (once generated) may not accurately reflect the current location of the identified anatomical features if motion is occurring. Thus, if motion is detected and the detected motion is predictable along a trajectory, the image that is input to the model may be adjusted so that the image reflects the predicted motion. Likewise, if motion is detected that is predictable (e.g., along a trajectory), the output of the model may be adjusted based on the detected motion before the output is fed back as an input to a subsequent iteration of the model, as explained below.

At 508, adjusted first output of the segmentation and tracking model is displayed on the display device along with a second ultrasound image. The first output of the model may be the output generated by the model using the first ultrasound image as input to the model. The first output may include identification of one or more anatomical features present in the first ultrasound image, including the location of each identified anatomical feature, the boundaries of each identified anatomical feature, and so forth. The first output may be used by the ultrasound system to generate annotations that may be displayed over the second ultrasound image, indicating the identity and location of each identified anatomical feature. The annotations may include, for each identified anatomical feature, a letter identifying that anatomical feature (e.g., an "A" to identify an artery, a "B" to identify a bone, a "V" to identify a vessel) placed at the centroid of the identified anatomical feature, an outline that follows and is overlaid on the boundary of the identified anatomical feature, a color tint that is overlaid on the identified anatomical feature, and/or another suitable representation of the location of the identified feature that may or may not include an indication of which type of anatomical feature has been identified. For example, when an anatomical feature is annotated with an outline, the color of the outline may be indicative of the type of anatomical feature (e.g., blue for bone, red for vessel), or each outline may be the same color and thus the type of anatomical feature may not be identified. The second ultrasound image may be acquired after the first ultrasound image. For example, as explained previously, the ultrasound system may acquire and display ultrasound images at a first frame rate, such as 30 Hz. The segmentation and tracking model may not generate output fast enough to segment and track identified anatomical features in real time, and thus by the time the first output is generated by the model, one or more additional ultrasound images may have already been acquired and displayed. Thus, the annotations generated based on the first output may be overlaid on a second, subsequent ultrasound image. Accordingly, the first output may be adjusted based on detected motion (e.g., motion that occurs between acquisition of the first ultrasound image and acquisition of the second ultrasound image), as explained above.

At 510, a third ultrasound image and the first output are entered as input to the model. By including the first output of the model as input to a subsequent iteration of the model (along with a subsequent ultrasound image), the tracking of identified anatomical features may be improved. For example, if the model knows, based on the output from the previous iteration of the model, the location of a given anatomical feature, the confidence of identifying the given anatomical feature in a subsequent image may be increased, and may allow for tracking of the given anatomical feature across multiple images even if the given anatomical feature would be difficult for the model to discern in a stand-alone image. In some examples, the third ultrasound image may be acquired after the second ultrasound image. In other examples, the third ultrasound image may be the second ultrasound image, e.g., the same image may be annotated with the first output and used as input for a subsequent iteration of the model. In some examples, the first output that is entered as input to the model may be the adjusted first output (e.g., adjusted based on detected motion).

Entering the third ultrasound image and the first output to the segmentation and tracking model may include, as indicated at 512, entering the first output as an input layer, such as a layer of the input image (e.g., as a layer of the third ultrasound image that is input to the model). For example, as shown in FIG. 3, the output of the model (e.g., the output layer 356a of the CNN 300) may be added to (e.g., concatenated with) the input image (e.g., the input image 302a) and entered together as input to the model. The first output, upon being generated, may be saved in a buffer and the buffered first output may be applied to the input layer of the model.

In some examples, entering the third ultrasound image and the first output to the segmentation and tracking model may include, as indicated at 513, entering the first output as a layer of the input image with the first image. For example, both the first output and the first image (which was entered to the model to generate the first output) may be saved in a buffer and the buffered first output and buffered first image may be applied to (e.g., concatenated with) the input layer of the model. By including both the first output and the first image used to create the first output as feedback to the model, the identification and tracking of the anatomical features in the third image may be improved.

In some examples, entering the third ultrasound image and the first output to the segmentation and tracking model may include, as indicated at 514, entering the first output into a bottom layer of the model. For example, as shown in FIG. 4, the output of the model (e.g., the output layer 356a of the CNN 400) may be added to (e.g., concatenated with) an aspect of the bottom layer (e.g., the feature map 326) of the model and the output and feature map may be convolved to form another feature map that eventually forms the output of the model (e.g., after various convolutions and up-convolutions are performed). The first output, upon being generated, may be down-sampled (e.g., to the resolution of the feature map 326) saved in a buffer and the buffered, down-sampled first output may be applied to the bottom layer of the model. The model may generate a second output based on the third ultrasound image and the first output.

At 515, method 500 optionally includes adjusting the second output of the model to compensate for motion. The motion detection and compensation performed at 515 may be similar to the motion detection and compensation performed at 507, e.g., the motion tracker may analyze the ultrasound images acquired between the third ultrasound image and a fourth ultrasound image (on which the annotations generated from the second output are displayed) to detect motion, and if motion is detected, the second output may be adjusted to compensate for the motion.

At 516, adjusted second output of the segmentation and tracking model is displayed on the display device with the fourth ultrasound image. The second output of the model may be the output generated by the model using the third ultrasound image as well as the first output as input to the model. The second output may include identification of one or more anatomical features present in the third ultrasound image, including the location of each identified anatomical feature, the boundaries of each identified anatomical feature, and so forth. The second output may be used by the ultrasound system to generate annotations that may be displayed over the fourth ultrasound image, similar to the annotations generated from the first output and explained above. The second output may be adjusted to compensate for motion occurring between the acquisition of the third image and the acquisition of the fourth image. In some examples, the annotations may be adjusted to reflect a level of confidence in the identification of the anatomical features and/or the tracked location of the anatomical features. For example, an anatomical feature tracked with a high level of confidence may be annotated with an outline having a first, higher weight, while an anatomical feature tracked with a low level of confidence may be annotated with an outline having a second, lower weight. The level of confidence in the identification/tracking of an anatomical feature may be determined based on the segmentation output before thresholding, in an example. For example, the model may output a plurality of pixels each having a value that reflects a calculation/prediction of whether or not that pixel is part of an anatomical feature, and all pixels having a value below a threshold may be "thresholded" out (e.g., given a pixel value of zero). The pixel values of the anatomical feature that are not thresholded out may be analyzed to determine the level of confidence, where the higher the pixel values, the higher the confidence is that the anatomical feature is accurate. Alternatively, if an identified anatomical feature is stable in location and shape/boundary, that feature may be given a higher confidence than a feature that is changing in location and shape/boundary.

The fourth ultrasound image may be acquired after the third ultrasound image, and thus the annotations generated based on the second output may be overlaid on a fourth, subsequent ultrasound image. In some examples, between when the first output is generated and when the second output is generated, the annotations that are generated based on the first output may be displayed on the display device while the model is generating the second output. Because the ultrasound images may be acquired at a rate that is faster than the segmentation and tracking model can generate its output, one or more intermediary ultrasound images may be obtained between the third ultrasound image and the fourth ultrasound image. These intermediary images may be displayed on the display device with the annotations that are generated based on the first output, which may be adjusted for motion as explained above.

In this way, the motion tracker and segmentation and tracking model may be used in parallel to accurately identify and track anatomical features across a plurality of images. The segmentation and tracking model may be accurate at identifying a variety of anatomical features in different views, but may experience delays due to the processing-intensive neural network used by the model. Thus, the segmentation and tracking model may act to "refresh" the location of tracked anatomical features at a low frame rate, such as once every five acquired ultrasound images. In between these resets/refreshes of the location of the tracked anatomical features, the motion tracker may act to fine-tune the locations of the tracked anatomical features. However, in some examples, the motion tracker may be omitted (or at least not utilized for the anatomical feature identification and tracking disclosed herein) and no adjustments to the model output/annotations generated based on separately detected motion may be made. Further, in examples where the segmentation and tracking model is able to generate output at the same frame rate (or faster) than the rate the ultrasound images are acquired, adjustments made in response to motion detection would be unnecessary and thus not performed. In these examples, the output that is generated by the model may be displayed with the same image used to generate the output rather than a later image.

Method 500 proceeds to 518, shown in FIG. 5B, to determine if a request to cease the segmentation has been received. The request to cease the segmentation may be received via user input or the request may be generated automatically based on a scanning workflow, similar to the request to initiate the segmentation described above at 504. If a request to cease the segmentation has been received, method 500 proceeds to 520 to display unsegmented images on the display device. For example, any subsequently acquired ultrasound images may be displayed without any corresponding annotations or indications of identified anatomical features. In some examples, the request to cease the segmentation may be in the form of powering off the ultrasound probe or otherwise terminating the current scanning session, in which case no additional ultrasound images may be displayed. Method 500 then returns.

If the request to cease segmentation is not received, method 500 proceeds to 522 to continue to display the output of the segmentation and tracking model with acquired ultrasound images on the display device, and provide the output as feedback to the model. For example, each fifth image (or other suitable interval of images) may be fed to the model and each iteration of output generated by the model may be used as feedback input to the next iteration of the model, as explained above at 510. As explained previously, this may include adjusting the visual representation of the output (e.g., the annotations that are displayed on the images) if motion is detected.

Further, in some examples, when annotations are displayed with an ultrasound image to indicate the identity and/or location of various anatomical features as determined from the segmentation and tracking model, the user who is viewing the images on the display device may enter input (e.g., via user interface 115) indicating the locations of the anatomical features (e.g., a correction of the location(s) if the location(s) is not accurate or a confirmation of a location (s)). The user input may be used by the segmentation and tracking model to determine if the output generated by the model is accurate and thus is acceptable to use as feedback to the model. For example, user confirmation of a location of an anatomical feature may change the certainty (intensity) of the confirmed feature. User correction of an anatomical feature location may cause removal of the previous output, and instigation of a "manual" high certainty output at the indicated corrected location. The system may then either enter the follow, track, and do not lose mode (practically inform when lost) or remain in the default mode after correction.

At 524, method 500 optionally includes notifying the operator of the ultrasound system if a tracked anatomical feature can no longer be reliably tracked. For example, the segmentation and tracking model may determine that a tracked anatomical feature, such as a bone, is starting to move out of the field of view of the ultrasound probe. A notification may be generated to inform the operator that the bone is partially or fully out of the field of view. The notification may include an adjustment to the visual appearance of the annotation for that bone, such as changing the color of the color tint, changing the color, weight, and/or dash pattern of the outline, etc. In other examples, the notification may include a text notification displayed on the display device warning the operator about the position of the bone (e.g., "the bone is moving out of the field of view"), an audio notification, haptic feedback, or other suitable notification. The determination that the tracked anatomical feature can no longer be reliably tracked may be based on the anatomical feature moving out of the field of view (as explained above), a change in the size/shape of the anatomical feature in an image such that the anatomical feature cannot be identified by the model, another object obscuring the anatomical feature (such as a needle being inserted), or virtually any other reason why the model may not be able to accurately determine the identity of the anatomical feature.

At 526, method 500 optionally includes adjusting one or more ultrasound imaging parameters based on the tracked anatomical features. For example, one or more of ultrasound transducer frequency, imaging depth, image gain, beam steering, and/or other imaging parameters may be automatically adjusted in order to maintain a tracked anatomical feature in view, to maintain a desired imaging plane of a tracked anatomical feature in view, etc. For example, if an anatomical feature of interest is moving up or down, the focus of the ultrasound probe may be adjusted to follow the anatomical feature. Additionally, frequency may be optimized to depth (e.g., higher frequency for shallower images).

It should be understood that 524 and/or 526 may be performed at any point during method 500 when it is determined that a feature can no longer be reliably tracked and/or when it is determined that imaging may be improved by adjusting the one or more imaging parameters. Further, 526 and/or 524 may be performed using other segmentation and/or tracking techniques, such as image processing techniques (e.g., edge detection).

Figure 6:
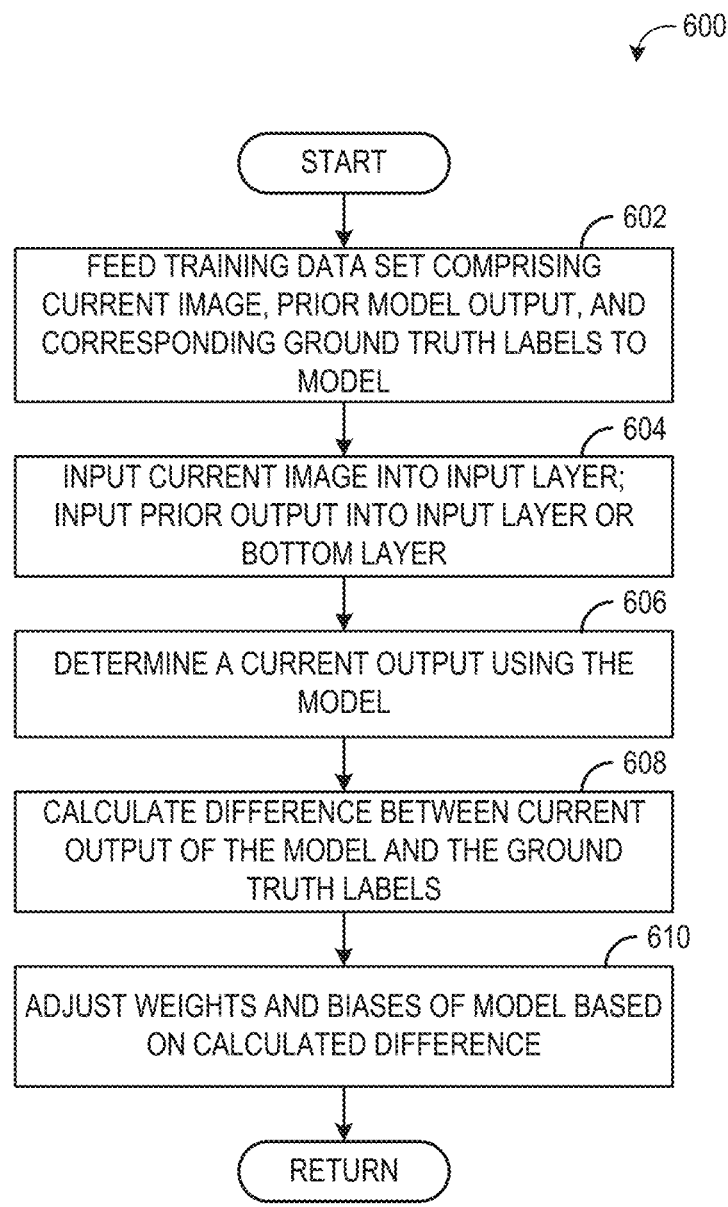
FIG. 6 is a flow chart illustrating a method for training the segmentation and tracking model, according to an exemplary embodiment.

Referring to FIG. 6, a flow chart of a method 600 for training a segmentation and tracking model (such as CNN 300 shown in FIG. 3) is shown, according to an exemplary embodiment. Method 600 may be implemented by training module 210.

At 602, a training data set, from a plurality of training data sets, is fed to the segmentation and tracking model, wherein the training data set includes a current ultrasound image, a prior model output, and corresponding ground truth labels. The prior model output may be determined based on a prior ultrasound image that is acquired immediately prior to the current ultrasound image, or from a prior image that is acquired before the current ultrasound image but with one or more intermediate ultrasound images acquired between the current ultrasound image and the prior ultrasound image. For example, the prior ultrasound image may be a first frame of ultrasound data collected by an ultrasound probe and the current ultrasound image may be a fifth frame of ultrasound data collected by the ultrasound probe, with the second, third, and fourth frames of ultrasound data collected by the ultrasound probe discarded for the purposes of the training data set.

As discussed previously, a ground truth may include an expected, ideal, or "correct" result from a machine learning model based on input of the current ultrasound image. In one example, in a machine learning model trained to identify anatomical features in ultrasound images, a ground truth output corresponding to a specific ultrasound image may include an expert curated segmentation map of the ultrasound image, which may include anatomical features segmented from background as well as labels identifying each anatomical feature. In another example, the ground truth output may be produced by an analytical method/algorithm. In this way, the ground truth labels may identify, for each image, the identity and location of each anatomical feature in each image. In some embodiments, the training data set, and the plurality of training data sets, may be stored in the image processing system, such as in MR image data 212 of image processing system 31. In other embodiments, the training data set may be acquired via communicative coupling between the image processing system and an external storage device, such as via Internet connection to a remote server.

At 604, the current image of the training data set is input into an input layer of the model. In some embodiments, the current image is input into an input layer of a CNN, having an autoencoder-autodecoder type architecture, such as CNN 300 shown in FIG. 3 or CNN 400 shown in FIG. 4. In some embodiments, each voxel or pixel value of the current image is input into a distinct node/neuron of the input layer of the model. The prior output of the training data set is input into either the input layer, along with the current image (as shown by CNN 300 of FIG. 3), or a bottom layer of the model (as shown by CNN 400 of FIG. 4). When the prior output is input into the input layer, the prior output may be at the same resolution as the current image. When the prior output is input into the bottom layer, the prior output may be down-sampled to a different (lower) resolution than the current image.

At 606, a current model output, indicative of the identity and location of one or more anatomical features in the current image, is determined using the current image, prior output, and the model. For example, the model may map the input current image to the identity and location of the anatomical features by propagating the input current image from the input layer, through one or more hidden layers, until reaching an output layer of the model. In some embodiments, the output of the model comprises a matrix of values, with each value corresponding to an identified anatomical feature (or lack of identified feature) at a respective pixel or voxel of the input current image.

At 608, the difference between the current output of the model and the ground truth labels corresponding to the current image is calculated by the image processing system. In some embodiments, a difference between each output value, corresponding to a predicted anatomical feature of the input current image and an anatomical feature indicated by the ground truth labels is determined. The difference may be calculated according to a loss function, for example:

$$\text{DICE} = (S \cap T)/(S \cup T),$$

wherein S is the ground truth labels and T is the predicted anatomical features. In other words, the output of the model may include, for each pixel or voxel of the input current image, an indication of which anatomical feature (or lack thereof) that pixel is part of. The ground truth labels may likewise include an indication, for each pixel of the current image, which identified anatomical feature that pixel is part of. The difference between each output value and the ground truth labels may then be determined.

At 610, the weights and biases of the model are adjusted based on the difference calculated at 608. The difference (or loss), as determined by the loss function, may be back propagated through the model (e.g., the neural learning network) to update the weights (and biases) of the convolutional layers. In some embodiments, back propagation of the loss may occur according to a gradient descent algorithm, wherein a gradient of the loss function (a first derivative, or approximation of the first derivative) is determined for each weight and bias of the model. Each weight (and bias) of the model is then updated by adding the negative of the product of the gradient determined (or approximated) for the weight (or bias) with a predetermined step size. Method 600 may then end. It will be noted that method 600 may be repeated until the weights and biases of the model converge, or the rate of change of the weights and/or biases of the model for each iteration of method 600 are under a threshold.

In this way, method 600 enables a model to be trained to predict the location and/or other attributes (e.g., identification) of one or more anatomical features from a current ultrasound image, thereby facilitating automatic determination identified anatomical features in subsequent ultrasound scans.

FIG. 7 shows a first set of ultrasound images 700 including a first image 710 that may be an image of internal structures of a patient acquired by an ultrasound probe at a first point in time and a second image 720 that may be an image of the internal structures of the patient acquired by the ultrasound probe at a second, later point in time. In one example, the first image 710 may be a first frame of ultrasound data and the second image may be a fifth frame of ultrasound data in a series of consecutively acquired frames of ultrasound data. As appreciated by first image 710 and second image 720, any relevant anatomical features in first image 710 and/or second image 720 may be difficult to discern. Additionally, subtle movement of one or more anatomical features from first image 710 to second image 720 may force a clinician viewing first image 710 and second image 720 in real time to keep his or her eyes fixed to the display device on which first image 710 and second image 720 are displayed in order to maintain identification of relevant anatomical features.

FIG. 8 shows a second set of ultrasound images 800 including a first image 810 and a second image 820. First image 810 and second image 820 may be the images of FIG. 7 annotated with outlines demarking identified anatomical features as determined from output of a segmentation and tracking model as described herein. For example, first image 710 may be input into the segmentation and tracking model (and optionally along with a prior output of the model, if the prior output is available) to generate the annotations overlaid on first image 810, and second image 720 may be input into the segmentation and tracking model along with the output of the model used to generate the annotations overlaid on first image 810, in order to generate the annotations overlaid on second image 820. In first image 810, three anatomical features are identified and labeled, including a first feature labeled by a first annotation 812, a second feature labeled by a second annotation 814, and a third feature labeled by a third annotation 816. In one non-limiting example, the first feature may be identified as a nerve, the second feature may identified as a bone, and the third feature may be identified as an artery.

As appreciated by second image 820, between the time when first image 810 was acquired and when second image 820 is acquired, each identified anatomical feature has shifted to the right, and thus each annotation shown in second image 820 has been adjusted in location relative to the annotations shown in first image 810. The first feature labeled by first annotation 812 has also morphed in shape, causing the first feature (e.g., the nerve) to shift upward and away from the second feature (e.g., the bone) and thus the first annotation 812 is adjusted in shape relative to the first annotation 812 shown in first image 810. This movement in the anatomical features may be hard to detect in the first set of images 700 shown in FIG. 7. By annotating the images with an indication of the location/extent of each identified anatomical feature as shown by the second set of images 800 of FIG. 8, a clinician may be able to easily track anatomical features even as the features shift in location and/or morph in size and/or shape, which may allow the clinician to look away from the images to attend to the patient or medical procedure without causing the clinician to lose orientation of the anatomical features when the clinician resumes looking at the images.

Figure 9:
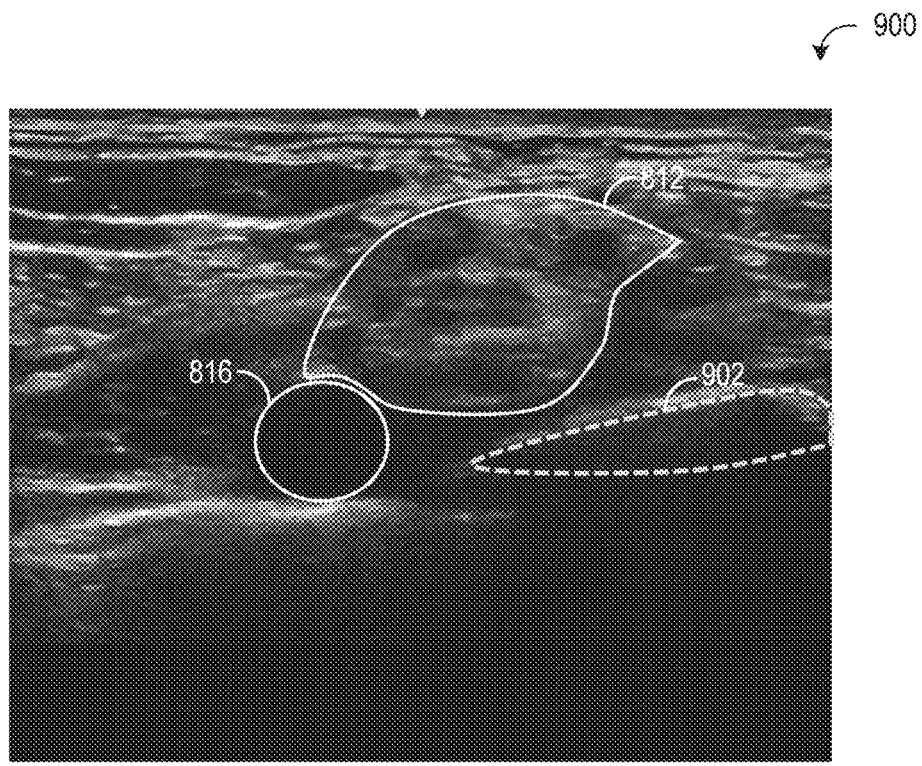
FIG. 9 shows a frame of ultrasound image data with identified features tracked and labeled, including a visual indication of a warning condition.

While the annotations shown in FIG. 8 include outlines overlaid on the boundaries of each anatomical feature, with the outlines having the same weight and color for each identified anatomical feature, other types of annotations are possible without departing from the scope of this disclosure. For example, the annotations may include a letter indicative of the type of anatomical feature (e.g., A for artery) overlaid on a center of each respective anatomical feature, which may allow more of the underlying image, including the boundaries of each identified anatomical feature, to be shown. In another example, the annotations may include a semi-transparent layer positioned over each respective identified anatomical feature, with each semi-transparent annotation having a size and shape that matches the underlying anatomical feature. In still other examples, annotations may include combinations of the above. Further, the color, line weight, dash pattern, and/or other parameters of the annotations may be adjusted to better differentiate neighboring anatomical features, provide information indicating a type of anatomical feature (e.g., arteries may be colored red while bones may be colored white), or alert a user/clinician of a warning condition, such as an identified anatomical feature moving out of the field of view or otherwise being unreliably tracked. For example, FIG. 9 shows an image 900 that includes second image 720 overlaid with a set of annotations, similar to second image 820. The annotations may include first annotation 812 labeling the first feature and third annotation 816 labeling the third feature, as shown in FIG. 8. However, the second feature may be labeled with annotation 902, which may have a dashed pattern line rather than a solid line. The dashed pattern line of annotation 902 may indicate that the second feature is starting to move of the field of view of the ultrasound probe, and thus the operator of the ultrasound system may see the dashed line and opt to adjust the position of the ultrasound probe to maintain the second feature fully in the field of view.

A technical effect of generating and displaying annotations on identified anatomical features of multiple successive ultrasound images is user tracking of anatomical features may be improved, which may improve patient care. A technical effect of using the output of a machine learning model as input to a subsequent iteration of the machine learning model is that the output may be more accurate and may allow for identification of anatomical features that may otherwise be undiscernible.

In another representation, a method includes adjusting a parameter of an annotation indicative of a current location of an identified anatomical feature in a current ultrasound image based on the current ultrasound image and a prior location of the identified anatomical feature in a prior ultrasound image, the annotation displayed on a display device. In an example, the method further includes identifying, via a segmentation and tracking model, the current location of the identified anatomical feature in the current ultrasound image using the current ultrasound image as a first input to the model and the prior location of the identified anatomical feature as a second input to the model.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
outputting, for display on a display device, an annotation indicative of a first location of an identified anatomical feature of a first ultrasound image, the annotation generated based on a first output of a model; and
outputting, for display on the display device, an adjusted annotation based on a second output of the model, the second output of the model generated by the model based on input including a second ultrasound image and the first output of the model, the adjusted annotation indicative of a second location of the identified anatomical feature in the second ultrasound image, wherein the second ultrasound image and the first output are entered at different layers of the model.

2. The method of claim 1, wherein the adjusted annotation is adjusted relative to the annotation in one or more of location, size, shape, and visual appearance.

3. The method of claim 1, wherein the adjusted annotation is adjusted relative to the annotation in a location of the annotation to reflect the identified anatomical feature moving from the first location to the second location, and further comprising if the second location is at least partially out of a field of view of an ultrasound probe used to acquire the second ultrasound image, also adjusting a visual appearance of the annotation.

4. The method of claim 1, wherein the first output of the model is generated using the first ultrasound image as input to the model, wherein the second ultrasound image is acquired after the first ultrasound image, and wherein the first output includes a probability, for each pixel of the second ultrasound image, that the pixel is part of the identified anatomical feature.

5. The method of claim 1, wherein the second ultrasound image and the first output are entered at a common input layer of the model and at a common resolution.

6. The method of claim 1, wherein the first output is entered at a lower resolution than the second ultrasound image.

7. The method of claim 1, wherein the second ultrasound image is entered at an input layer of the model and the first output is entered at a bottom layer of the model.

8. A method, comprising:
inputting a first ultrasound image into a segmentation and tracking model;
receiving, as a first output from the segmentation and tracking model, a first location of an identified anatomical feature in the first ultrasound image;
displaying, on a display device, a first annotation at the first location on a second ultrasound image;
inputting the second ultrasound image and the first output into the segmentation and tracking model;
receiving, as a second output from the segmentation and tracking model, a second location of the identified anatomical feature in the second ultrasound image; and
displaying, on the display device, a second annotation at the second location on a third ultrasound image, wherein the segmentation and tracking model comprises a convolutional neural network having an input layer and an output layer, wherein the first output is output from the output layer, and wherein the second ultrasound image and the first output are entered into the convolutional neural network at the input layer.

9. The method of claim 8, wherein the second ultrasound image is acquired after the first ultrasound image and the third ultrasound image is acquired after the second ultrasound image.

10. The method of claim 9, wherein one or more additional ultrasound images are acquired between acquisition of the second ultrasound image and acquisition of the third ultrasound image, and wherein the first annotation is displayed on the display device with each of the one or more additional ultrasound images.

11. The method of claim 10, further comprising determining, using a motion tracker, that motion of the identified anatomical feature is present across the second ultrasound image and the one or more additional ultrasound images, and in response, adjusting the first annotation based on the determined motion.

12. The method of claim 8, further comprising adjusting one or more ultrasound imaging parameters of an ultrasound probe used to acquire the first ultrasound image, the second ultrasound image, and the third ultrasound image based at least in part on the first output and/or the second output.

13. The method of claim 12, wherein the one or more ultrasound imaging parameters comprise one or more of frequency, depth, and gain.

14. The method of claim 8, wherein displaying the first annotation at the first location on the second ultrasound image comprises displaying the first annotation as an overlay on the identified anatomical feature in the second ultrasound image.

15. A system, comprising:
an ultrasound probe;
a memory storing instructions; and
a processor communicably coupled to the memory and when executing the instructions, configured to:
acquire, via the ultrasound probe, a first ultrasound image;
identify, via output from a model, one or more anatomical features present in the first ultrasound image;
acquire, via the ultrasound probe, a second ultrasound image; and
determine a respective location of each of the identified one or more anatomical features in the second ultrasound image via the model using the second ultrasound image as input to the model and using the output as feedback to the model, wherein the model is a convolutional neural network (CNN), wherein the output is an output layer of the CNN, and wherein the output is entered to the CNN at an input layer of the CNN with the second ultrasound image.

16. The system of claim 15, further comprising a display device, and wherein, when executing the instructions, the processor is configured to output, to the display device, one or more annotations each representing a respective location.

17. The system of claim 15, wherein when executing the instructions, the processor is configured to output, to the display device, a third ultrasound image acquired after the second ultrasound image, the one or more annotations displayed on the third ultrasound image.

18. The system of claim 15, wherein the output and the second ultrasound image are formed as a vector that is entered at the input layer of the CNN.

* * * * *